United States Patent [19]

Yoshida

[11] 4,246,606
[45] Jan. 20, 1981

[54] INSPECTION APPARATUS

[75] Inventor: Hajime Yoshida, Tokyo, Japan

[73] Assignee: Hajime Industries Ltd., Tokyo, Japan

[21] Appl. No.: 30,853

[22] Filed: Apr. 17, 1979

[51] Int. Cl.$^3$ .............................................. H04N 7/18
[52] U.S. Cl. ................................................... 358/106
[58] Field of Search ............... 358/106, 280, 282, 163;
250/562, 563; 340/146.3 H

[56] References Cited
U.S. PATENT DOCUMENTS

| | | | |
|---|---|---|---|
| 3,626,092 | 12/1971 | Wilson | 358/280 |
| 3,781,531 | 12/1973 | Baker | 250/562 |
| 3,889,053 | 6/1975 | Lloyd et al. | 358/106 |
| 3,916,439 | 10/1975 | Lloyd et al. | 358/106 |
| 3,952,144 | 4/1976 | Kolker | 358/282 |
| 3,962,681 | 6/1976 | Requa et al. | 340/146.3 H |
| 4,072,928 | 2/1978 | Wilder | 340/146.3 H |

Primary Examiner—Howard W. Britton
Assistant Examiner—Joseph A. Orsino, Jr.
Attorney, Agent, or Firm—Thomas R. Morrison

[57] ABSTRACT

An inspection apparatus for inspecting an object is disclosed, in which an object to be inspected and/or a reference body are picked up by an image sensing device such as a television camera and an output video signal from the television camera is processed by a video signal processing circuit. In this case, a reference or calibration body is located within a visual field of the television camera and picked up by the television camera together with said reference body and/or calibration body under the irradiation of light, a signal corresponding to the calibration body included in the video signal from the television camera is detected and this detected signal is used to correct the video signal. The corrected video signal is applied to a computer to judge whether the object is same as the reference body or not.

6 Claims, 10 Drawing Figures

INSPECTION APPARATUS

BACKGROUND OF THE INVENTION

1. Field of the Invention

The present invention relates generally to an inspection apparatus for inspecting the shape and so on of an object to be inspected, and is directed more particularly to an inspection apparatus which can accurately inspect an object steadily regardless of variations or fluctuations of the circumstance around the object and fluctuations in the function of the inspection apparatus itself.

2. Description of the Prior Art

Figure 1:
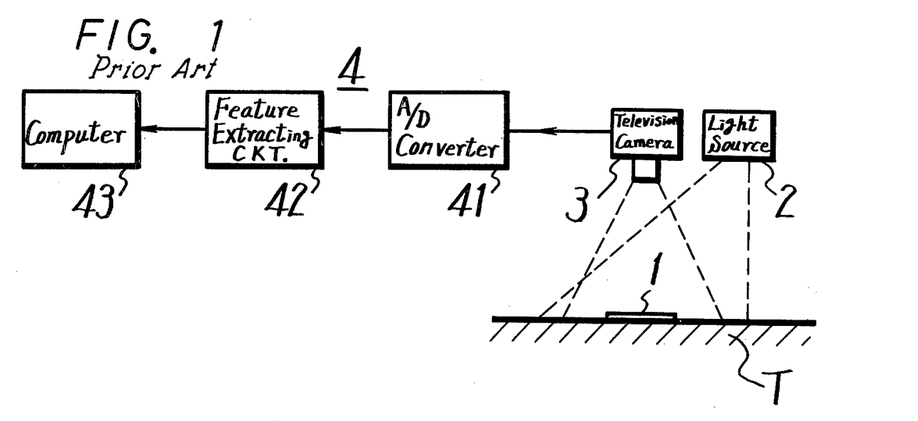
FIG. 1 is a block diagram showing an example of the prior art inspection apparatus.

In the prior art inspection apparatus of this kind, as shown in FIG. 1, for instance, a body which will be a standard i.e. becomes a reference body 1 for the following inspection, is located on inspection table T. While this reference body 1 is irradiated with the light from a light source 2, the reference body 1 is picked up by a television camera 3. The video signal from the television camera 3 is fed to a video signal processing device or circuit 4, which includes an A/D (analog to digital) converter 41 and a device or circuit 42 which extracts the features of the video signal to be processed. The output information or signal therefrom is fed to, for example, a computer 43 as a reference information signal for the following inspection which is memorized therein.

Then, an object to be inspected is located on the inspection table T at the same position as that at which the reference body 1 was located (therefore, the object is shown by the same reference numeral 1 as the reference body in FIG. 1). Then, the object 1 is picked up by the television camera 3 while being irradiated with the light from the light source 2. This video signal from the television camera 3 corresponding to the object 1 is similarly processed by the video signal processing circuit 4, and the output information signal therefrom is fed to the computer 43. This output information signal from circuit 4 corresponding to the object 1 is compared in the computer 43 with the reference information signal stored therein and then it is judged by the computer 43 whether the object is same as the reference body or not, or whether the object is good or not.

With the above prior art inspection apparatus, due to the fact that, during inspection of objects 1, the intensity or amount of the light irradiated on the objects from the light source 2 maybe different from that irradiated on the reference body 1 when it is picked up and/or due to the drift of the electric circuitry or circuit system including the television camera 3 and so on, the video signal from the television camera 3 which picks up the object 1 may become different from that corresponding to the reference body 1 even through the object is the same as the reference body. Thus, although the object is the same as the reference body, erroneous judgements that the former differs from the latter may occur.

In general, it is ordinary that the light source 2 is subjected to secular change or the circumferential light of the objects 1 is varied and hence the amount or intensity of the light irradiated on the object 1 is varied to an extent which can not be neglected through time lapse. Further, drift frequently occurs in the electric circuit system of the television camera 3 and so on. Therefore, in the prior art inspection apparatus the erroneous judgement set forth above inevitably appears frequently which is a fatal defect for such inspection apparatus.

OBJECTS AND SUMMARY OF THE INVENTION

Accordingly, it is an object of the present invention to provide an inspection apparatus for an object free from the above mentioned defects encountered in the prior art inspection apparatus.

It is another object of the invention to provide an inspection apparatus which automatically and accurately corrects the difference appearing between the light amounts or intensities upon picking up a reference body and an object to be inspected by a television camera to perform accurate inspection of the object.

It is a further object of the invention to provide an inspection apparatus by which even if the circumferential lights upon picking a reference body and an object to be inspected are different, this difference is automatically and accurately corrected.

It is a yet further object of the invention to provide an inspection apparatus by which even if drifts and so on are caused by temperature variation and so on in the electrical circuit system including a television camera, its amplifier etc., the drifts and so on can be automatically and positively corrected to perform the inspection of an object accurately.

According to an aspect of the present invention, an inspection apparatus is provided which comprises an image sensing device for picking up a reference body and/or object to be inspected and for producing video signals of the reference and/or object, a light source for irradiating a visual field of the image sensing device within which the reference body and/or object is located, a calibration body located within the visual field of the image sensing device for the reference body, object and calibration body, the calibration body being picked up by the image sensing device together with the reference body and/or object and serving as a reference for inspection of the object when the object is picked up, a circuit for detecting a signal corresponding to the calibration body which is contained in the video signal corresponding to the object from the image sensing device and correcting the video signal with such detected signal, and a device for comparing the corrected video signal corresponding to the object with the video signal corresponding to the reference body to judge whether the object is the same as said reference body or not.

The other objects, features and advantages of the present invention will become apparent from the following description taken in conjunction with the accompanying drawings through which the like references designate the same elements.

DESCRIPTION OF THE PREFERRED EMBODIMENTS

The present invention will be hereinafter described with reference to the attached drawings.

A first example of the invention will be described with reference to FIGS. 2 to 5 in which the same reference numerals as those used in FIG. 1 designate the same elements.

Figure 2:
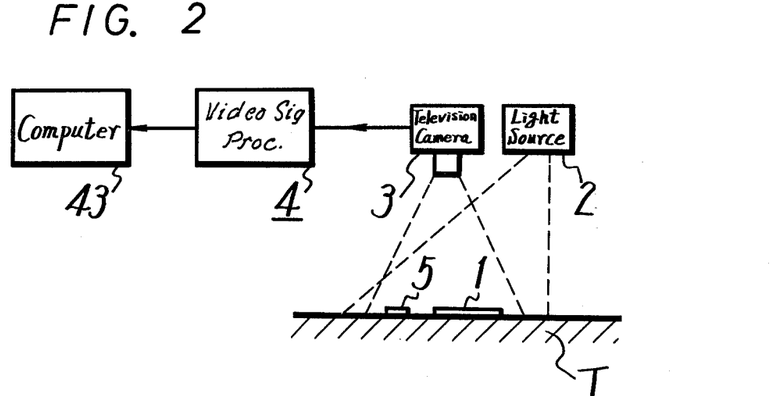
FIG. 2 is a schematic block diagram showing an embodiment of the inspection apparatus according to the present invention.
Figure 3:
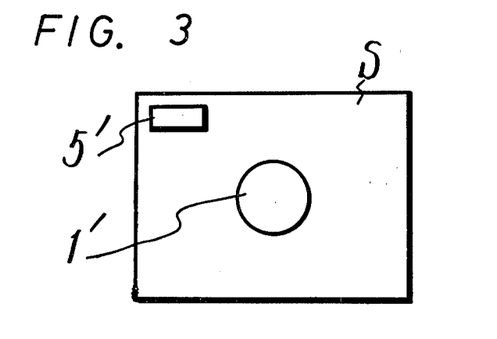
FIG. 3 is a schematic front view of the screen of an image sensing device such as a television camera used in the embodiment of the invention shown in FIG. 2.
Figure 4:
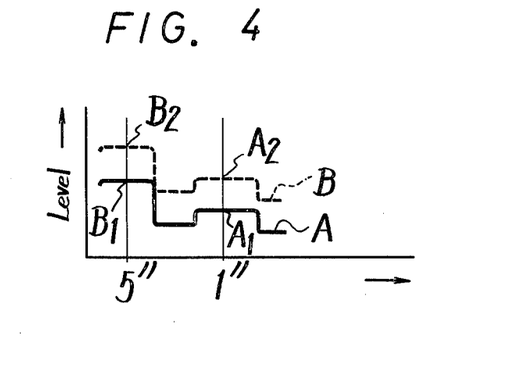
FIG. 4 is a waveform diagram showing video signals delivered from the television camera.

With the first example of the invention, when a reference body 1 is picked up by an image sensor such as a television camera 3, a reference or calibration body 5 such as a white paper is positioned near the reference body 1 on the inspection table T in the visual field of the television camera 3 as indicated by the dotted lines in FIG. 2. This calibration body 5 is used as a reference for the brightness in the visual field in the later inspection of an object. When the calibration body 5 and reference body 1 are picked up by the television camera 3, the picked-up pattern on its screen S becomes as shown in FIG. 3. In FIG. 3, reference 1' indicates the image of the reference body 1 and 5' an image of the calibration body 5, respectively. In this case, the video signal from the television camera 3 has a waveform indicated by, for example, the solid line curve A in FIG. 4. In the waveform diagram of FIG. 4, references 5" and 1" on the abscissa correspond to the substantial center positions of the image 5' of the calibration body 5 and the image 1' of the reference body 1, respectively, and references B1 and A1 indicate the levels of the video signal corresponding to the images 5' and 1', respectively. The video signal from the television camera 3 indicated by the solid line curve A in FIG. 4 is processed by a video signal processing circuit 4 in the manner similar to the prior art, and then fed to a computer 43, and then memorized therein as a reference or standard information signal for the following inspection of an object.

Next, when an object is inspected by the inspection apparatus of the invention, the calibration body 5 is located on the inspection table T at the same position as that upon picking up the reference body 1 and the object is positioned in place of the reference body 1 or at the same position as the reference body 1 on the inspection table T (accordingly, the object to be inspected is indicated at reference 1 similar to the reference body 1). Then, the calibration body 5 and object 1 located as above are both picked up by the television camera 3 while they are irradiated by the light from the light source 2. In this case, it will be apparent that the image on the screen S of the television camera 3 becomes the same as that shown in FIG. 3 in positions corresponding to the case of picking up the reference body 1 and the calibration body 5 as described above. If it is assumed that the object 1 is the same as the reference body 1 in appearance or the like, the brightness or intensity of the light in the visual field of the television camera 3 is the same while picking the reference body and the object, and the electrical circuit system of the camera 3 and operates the same as when picking up the reference body and the object, the video signal from the camera 3 is the same as indicated by the solid line curve A in FIG. 4. Therefore, correct judgement by the computer 43 will be made. In practice, however, since the light from the light source 2 may vary in amount or intensity and the electrical circuit system of the camera 3 and so on may drift as set forth above, even if the object and the reference body are the same, are located at the same position and they are picked up by the television camera 3, the video signal delivered from the camera 3 is different from that A upon picking up the reference body 1 as indicated by, for example, a dotted line curve B in FIG. 4. Thus, if the video signal B is fed, without compensation for the change, to the video signal processing circuit 4 and then to the computer 43 to be inspected, the object may be judged as a reject or not same as the reference body.

Figure 5:
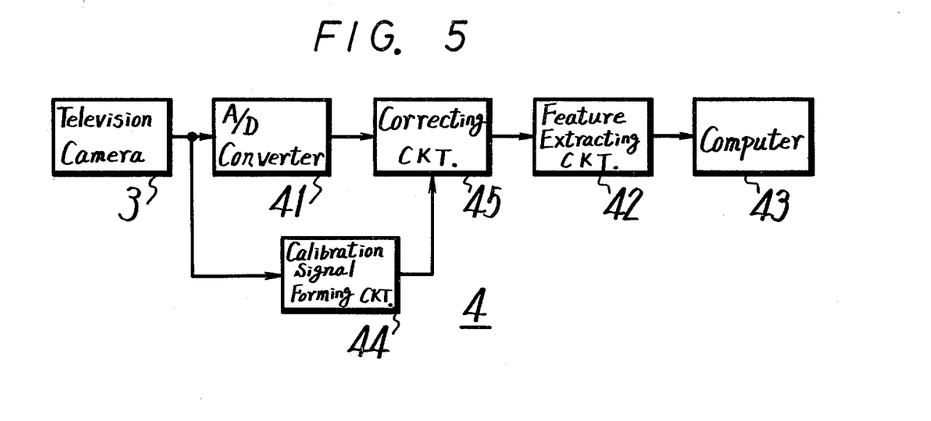
FIG. 5 is a systematic block diagram showing the main part of the invention shown in FIG. 2.

In order to avoid the above erroneous judgement, the video signal processing circuit 4 of the invention is formed as shown in FIG. 5. In the example of the video signal processing circuit 4 of the invention shown in FIG. 5, the output video signal from the television camera 3 is fed to an A/D converter 41 similar to the prior art and also to a calibration signal forming circuit 44 which will detect, for example, a signal corresponding to the calibration body 5 included in the video signal and provide a calibration signal based upon the detected signal such as a calibration signal corresponding to the level of the image 5' of the calibration body 5. The digital video signal from the A/D converter 41 and the calibration signal from the calibration signal forming circuit 44 are both applied to a correcting circuit 45. This correcting circuit 45 will correct the digital video signal from the A/D converter 41 with the calibration signal from the calibration signal forming circuit 44 in the following manner. That is, when the reference body 1 and the calibration body 5 are picked up by the television camera 3, its output video signal is as represented by the solid line curve A in FIG. 4 and the levels of the video signal corresponding to the reference body 1 and calibration body 5 are A1 and B1 in FIG. 4, respectively. However, when an object, which is same as the reference body 1, and the calibration body 5 located on the table T at the same position as the reference body 1 are picked up by the camera 3, its output video signal becomes as represented by, for example, the dotted line curve B in FIG. 4 due to the causes set forth previously, and the levels of the video signal corresponding to the object 1 and the calibration body 5 are changed to those A2 and B2 in FIG. 4, respectively. The correcting circuit 45 achieves such a correction that the level variation represented by the dotted line curve B is returned to the level of the solid line curve A i.e. the level B2 is returned to the level B1 to bring the video signal B entirely to the same level as the video signal A (in this case, the level A2 is of course returned to the level A1). In other words, the correcting circuit 45 makes the output level upon picking up the object equal to that upon picking up the reference body 1. The output from the correcting circuit 45 is applied to a feature extracting circuit 42 and the output therefrom is fed to the computer 43 to achieve the comparison of the information signal of the object with that of the reference body. Therefore, in the case that an object the same as the reference body is picked up by the television camera, even if the corresponding video signal from the camera is different from the video signal A of the reference body due to the above causes as indicated by the dotted line curve B in FIG. 4, the video signal B is made same as the video signal A by the calibration signal forming circuit 44 and correcting circuit 45, and hence the object can be judged to be the same as the reference body by the inspection apparatus of the present invention.

The inspection apparatus according to the present invention judges an object bad only when the object is truly different from the reference body (in this case, the video signal of the object itself of course differs from that of the reference body) and avoids an erroneous judgement from a cause other than the nature of the objects to be inspected as occurs in the prior art inspection apparatus.

In the example of the invention shown in FIG. 5, the correcting circuit 45 is provided after the A/D converter 41, correcting circuit 45 is not limited to a position after the A/D converter 41 as in the above example, but instead the correcting circuit 45 can be located elsewhere in the circuit without departing from the scope of the invention.

Figure 6:
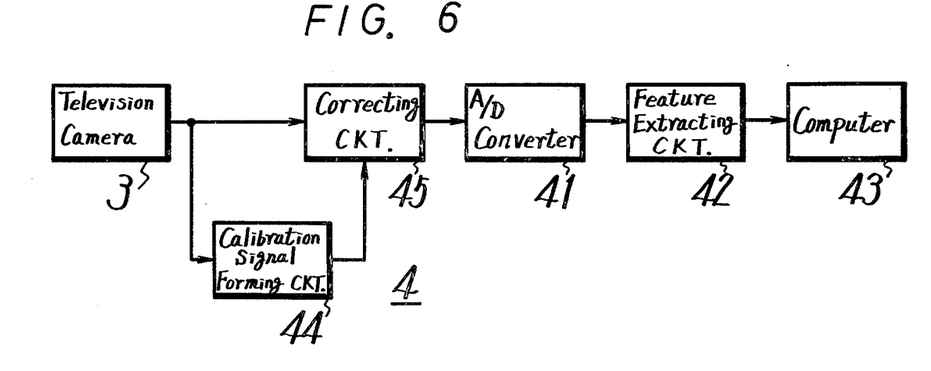
FIGS. 6 and 7 are systematic block diagrams respectively showing the main parts of other embodiments of the invention.

FIG. 6 is a block diagram showing the main part of another example of the present invention i.e. another example of the video signal processing circuit 4 of the invention. In FIG. 6, the parts or elements corresponding to those used in FIG. 5 are marked with the same numerals and their detailed description will be omitted.

In the example of the invention shown in FIG. 6, the output video signal from the television camera 3 is fed firstly to the calibration signal forming circuit 44 and also to the correcting circuit 45, and the output calibration signal from the circuit 44 is applied to the correcting circuit 45 to thereby normalize the video signal from the camera 3 in the correcting circuit 45 similar to the example shown in FIG. 5. That is, this example of FIG. 6 also provides a video signal which is free from the influences of variations in the light irradiated on the calibration body 5 and object and from the drift of the electrical circuit system including the camera etc. This video signal is processed through the A/D converter 41, feature extracting circuit 42 and the computer 43 similar to the above example of the invention to carry out the inspection of the object with the same effect as that of the above example of the invention.

Figure 7:
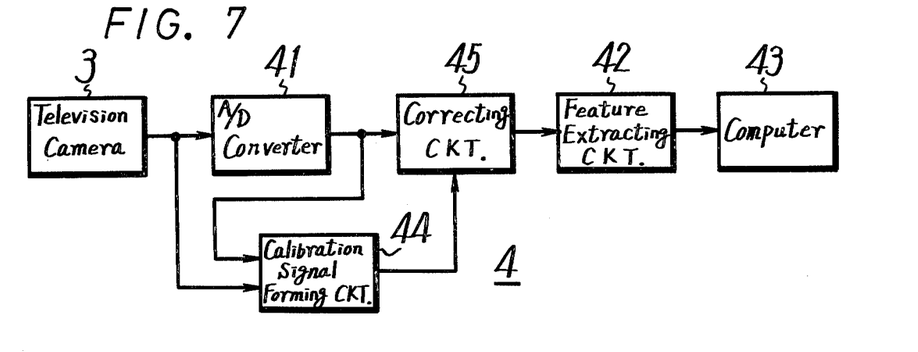

FIG. 7 shows a further example of the invention in which the same reference numerals as those used in FIGS. 5 and 6 designate the same elements and their detailed description will be omitted.

In the example of FIG. 7, the output video signal from the television camera 3 is applied to the A/D converter 41 and also to the calibration signal forming circuit 44 which is also supplied with the digital signal from the A/D converter 41, and the digital signal from the A/D converter 41 and the calibration signal from the circuit 44 are applied to the correcting circuit 45 whose output is processed by the circuit 42 and then fed to the computer 43 similar to the examples of FIGS. 5 and 6.

Next, practical examples of the video signal processing circuit 4 used in the examples of the invention shown in FIGS. 5, 6 and 7 will be described with reference to FIGS. 8, 9 and 10, respectively, in which the same reference numerals as those used in FIGS. 5, 6 and 7 designate the same parts.

Figure 8:
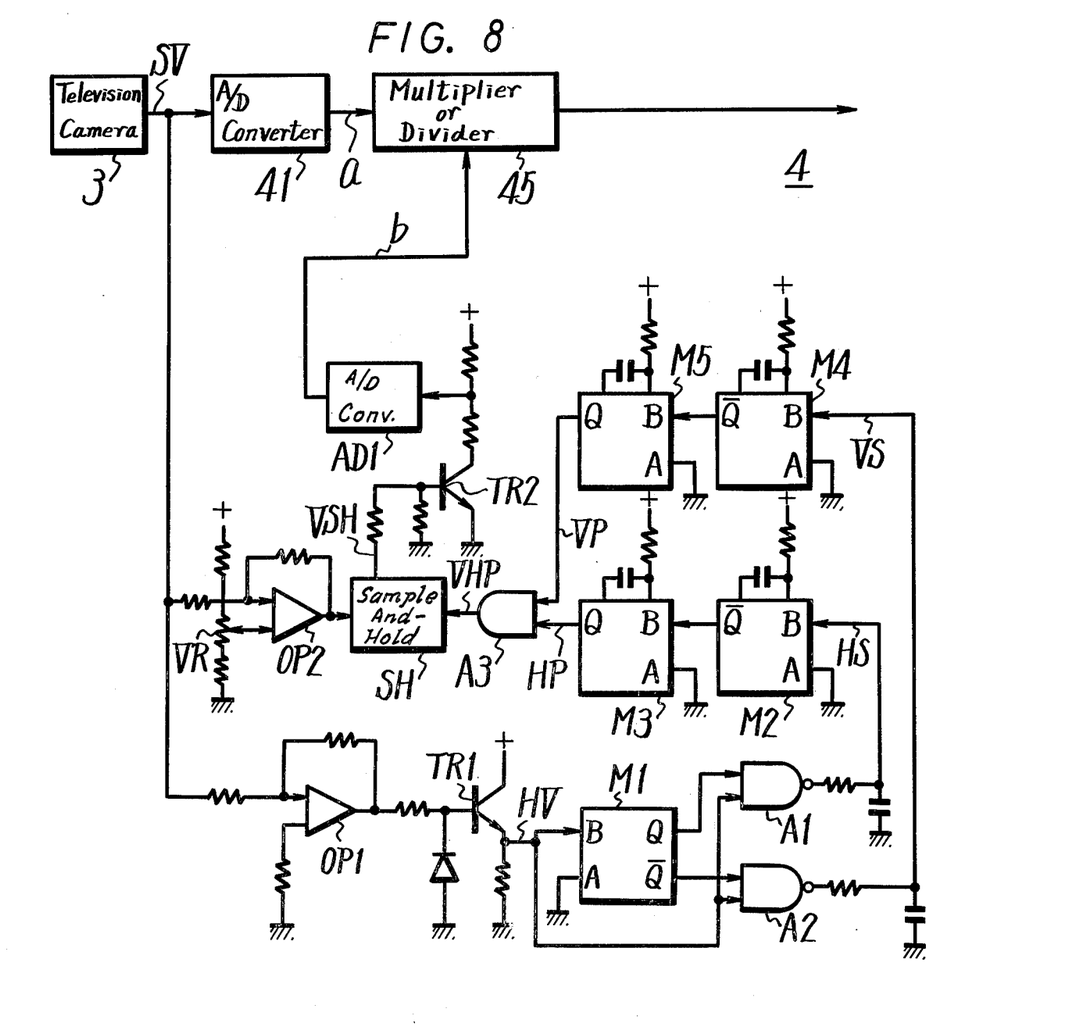
FIGS. 8, 9 and 10 are respectively detailed block and schematic diagrams showing practical examples of the main parts of the examples shown in FIGS. 5, 6 and 7.

FIG. 8 shows a practical example of the video signal processing circuit 4 used in the example of the invention shown in FIG. 5. In the practical example of FIG. 8, the composite video signal SV from the television camera 3 is applied through an operational amplifier OP1 to a transistor TR1 of the emitter follower configuration to produce a composite synchronizing signal HV at the emitter of the transistor TR1. This composite synchronizing signal HV is applied to a mono-stable multivibrator M1 and to NAND-circuits A1 and A2 which are also supplied with the outputs of multivibrator M1 to produce horizontal and vertical synchronizing signals HS and VS from the NAND-circuits A1 and A2, respectively. The horizontal synchronizing signal HS from the NAND-circuit A1 is applied to mono-stable multivibrators M2 and M3 to provide a synchronizing signal HP which will appoint the horizontal position of the calibration body 5 on the screen S, while the vertical synchronizing signal VS from the NAND-circuit A2 is applied to mono-stable multivibrators M4 and M5 to provide a synchronizing signal VP which will appoint the vertical position of the calibration body 5 on the screen S. In fact, since the video signal of the calibration body 5 appears at a position (time period) appointed by the synchronizing signals HP and VP, the signals HP and VP are fed to an AND-circuit A3 to provide a signal VHP which represents the above horizontal and vertical positions (time periods) of the video signal of the calibration body 5.

The video signal SV from the camera 3 is also fed to an operational amplifier OP2 whose output is fed to a sampling hold circuit SH which is also supplied with the signal VHP from the AND-circuit A3 and which samples and holds the video signal SV within a time period determined by the signal VHP applied thereto from the AND-circuit A3 to produce a sampling hold signal VSH. This signal VSH from the sampling hold circuit SH is fed to a transistor TR2 and then to an A/D converter AD1 which then produces a corresponding digital value b. The A/D converter 41, which is supplied with the video signal SV from the camera 3 as set forth previously, produces a corresponding digital value a. Both the digital values a and b are fed to a divider (correcting circuit) 45 which then calculates a/b. If the light introduced into the camera 3 upon the inspection of objects is decreased by, for example, 10% as compared with the picking up of the reference object and hence the digital value from the A/D converter 41 becomes 0.9a, the signal VSH from the sampling hold circuit SH is also decreased similarly and hence the digital value b from the A/D converter AD1 becomes 0.9b. Thus, the divider 45 calculates 0.9a/0.9b which is equal to a/b. The output from divider 45 is free from the influence of variations in the amount or intensity of light in the visual field of the television camera 3 and drift in the circuit system of the television camera 3 and so on.

In FIG. 8, reference letters VR designate a variable resistor which is connected to the operational amplifier OP1 at its input side to set the operation point thereof.

Figure 9:
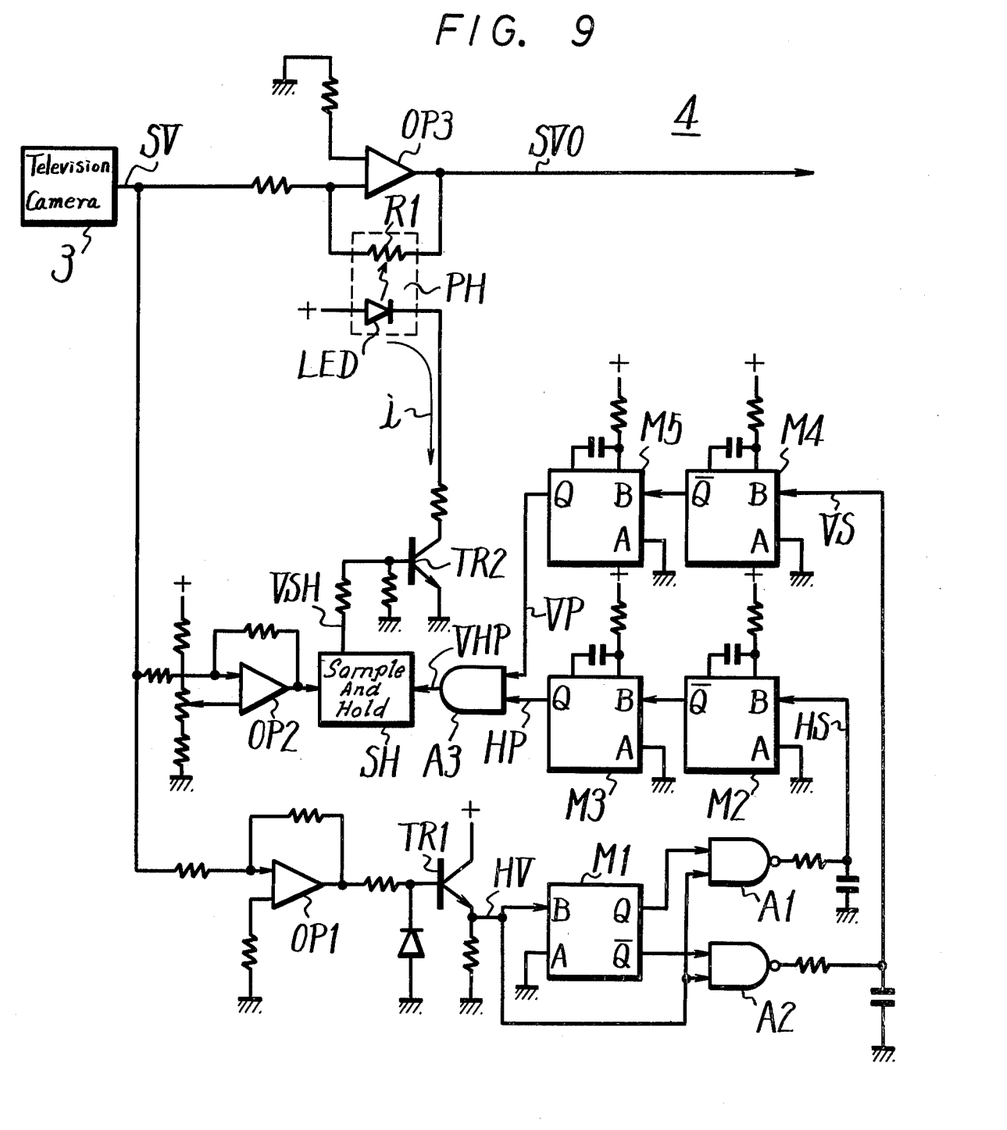

FIG. 9 shows a practical example of the video signal processing circuit 4 used in the example of the invention shown in FIG. 6. In the practical example of FIG. 9, the composite video signal SV from the television camera 3 is applied through an operational amplifier OP1 to a transistor TR1 of the emitter follower configuration to produce a composite synchronizing signal HV at the emitter of the transistor TR1. This composite synchronizing signal HV is applied to a mono-stable multivibrator M1 and to NAND-circuits A1 and A2 which are also supplied with the outputs of multivibrator M1 to produce horizontal and vertical synchronizing signals HS and VS from the NAND-circuits A1 and A2, respectively. The horizontal synchronizing signal HS from the NAND-circuit A1 is applied to mono-stable multivibrators M2 and M3 to provide a synchronizing signal HP which will designate the horizontal position of the calibration body 5 on the screen S, while the vertical synchronizing signal VS from the NAND-circuit A2 is applied to mono-stable multivibrators M4 and M5 to provide a synchronizing signal VP which will designate the vertical position of the calibration body 5 on the screen S. In fact, since the video signal of the calibration body 5 appears at a position (time period) designated by the synchronizing signals HP and VP, the signals HP and VP are fed to an AND-circuit A3 to provide a signal VHP which represents the above horizontal and vertical positions (time periods) of the video signal of the calibration body 5.

The video signal SV from the camera 3 is also fed to an operational amplifier OP2 whose output is fed to a sampling hold circuit SH which is also supplied with the signal VHP from the AND-circuit A3 and samples and holds the video signal SV within a time period determined by the signal VHP applied thereto from the AND-circuit A3 to produce a sampling hold signal VSH. This signal VSH is fed to a transistor TR2 whose output side is connected to a light emitting diode LED of a photo-coupler PH which also includes a photoelectric conversion element or resistor such as R1. The resistor R1 of the photo-coupler PH is connected across an operational amplifier OP3 which is supplied with the video signal SV from the camera 3. When the signal VSH is high in level, a current i flowing through the diode LED of the photo-coupler PH increases. Thus, the resistance value of the resistor R1 of the photo-coupler PH decreases at this time. When the resistance value of the resistor R1 decreases, the amplification factor of the operational amplifier OP3 becomes low.

As described above, as the amplitude of the composite video signal SV increases, the amplification factor of the operational amplifier OP3 decreases, while as the video signal SV decreases, the amplification factor of the operational amplifier OP3 increases. As a result, the operational amplifier OP3 always produces a substantially constant output signal SVO which is fed to the A/D converter 41. Thus, the output from the circuit 45 is not influenced by variations in the amount of light in the visual field of camera 3 or by the drifts in the circuit system including camera 3 and so on similar to the example of FIG. 8.

Figure 10:
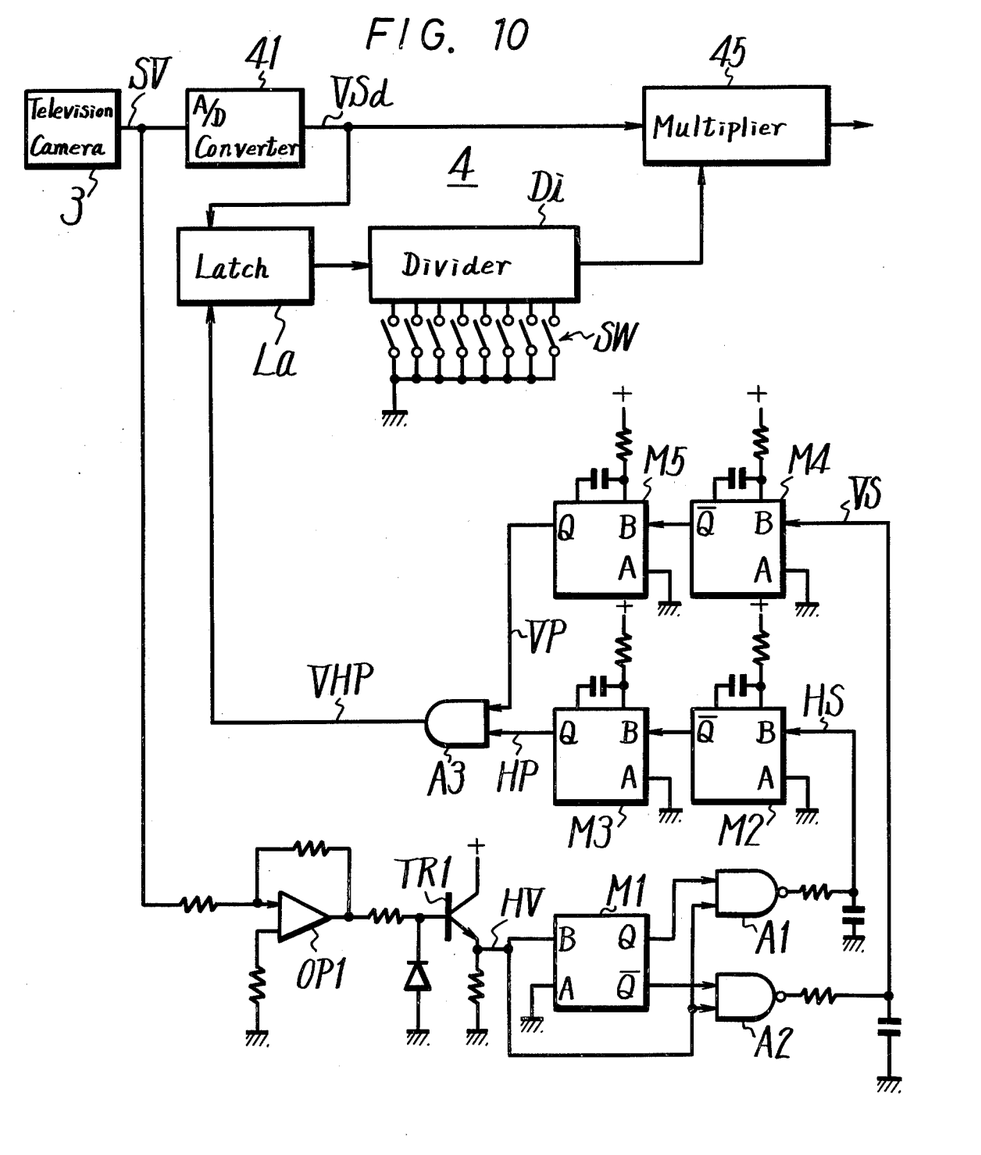

With reference to FIG. 10, a practical example of the circuit 4 used in the example of FIG. 7 will be described. In the example of FIG. 10, the composite video signal SV from the television camera 3 is applied through an operational amplifier OP1 to a transistor TR1 of the emitter follower configuration to produce a composite synchronizing signal HV at the emitter of the transistor TR1. This composite synchronizing signal HV is applied to a mono-stable multivibrator M1 and to NAND-circuits A1 and A2 which are also supplied with the outputs of multivibrator M1 to produce horizontal and vertical synchronizing signals HS and VS from the NAND-circuits A1 and A2, respectively. The horizontal synchronizing signal HS from the NAND-circuit A1 is applied to mono-stable multivibrators M2 and M3 to provide a synchronizing signal HP which will designate the horizontal position of the calibration body 5 on the screen S, while the vertical synchronizing signal VS from the NAND-circuit A2 is applied to mono-stable multivibrators M4 and M5 to provide a synchronizing signal VP which will designate the vertical position of the calibration body 5 on the screen S. In fact, since the video signal of the calibration body 5 appears at a position (time period) designated by the synchronizing signals HP and VP, the signals HP and VP are fed to an AND-circuit A3 to provide a signal VHP which represents the above horizontal and vertical positions (time periods) of the video signal of the calibration body 5. The signal VHP is applied to a latch circuit La to which the digital video signal VSd from the A/D converter 41. The output from the latch circuit La is fed to a divider Di to which a factor selecting switch SW is associated. The selecting switch SW has a plurality of switch elements for setting a suitable factor b for divider Di. The digital video signal VSd from the A/D converter 41 and the output signal from the divider Di are fed to the correcting circuit or multiplier 45.

It is assumed that when the reference body is picked up by the television camera 3, the A/D converter 41 produces digital video signals VSd or a1, - - - ai, - - - an in one frame period. In the latch circuit La which is supplied with the signals a1, - - - ai, - - - an and also with the signal VHP from the AND-circuit A3, if the digital video signal, for example, ai is latched in response to the signal VHP, the latch circuit La delivers the signal ai to the divider Di throughout one frame period. At this time, if a suitable factor bi is manually set by the switch SW for the divider Di in consideration of the characteristic of A/D converter 41, the divider Di produces an output of $c = b/a$ or $ci = bi/ai$. The output $ci = bi/ai$ is then fed to the correcting circuit or multiplier 45 which is also supplied with the output video signal VSd or a1, - - - ai n from the A/D converter 41 and hence which produces a corrected output signal with the calibration of $d = a \times c = (ai \ldots an) \times bi/ai$.

Next, when an object to be inspected is picked up by the television camera 3, and hence A/D converter 41 produces digital video signals a11, - - - a1i, - - - a1n. In this case, since the digital signal a1i is latched in the latch circuit La by the signal VHP (which is same as that produced upon picking up the reference object) and the factor bi is not changed, the output from divider Di is $c = bi/a1i$ and the corrected output from the multiplier 45 is $d = (ai - - - an) \times bi/a1i$. Thus, it will be clearly understood that the output from the multiplier 45 is not influenced by the variation in the light amount in the visual field of camera 3 and by the drifts in the circuit similar to the foregoing examples.

As described above, according to the present invention, even if a circumferential condition where an object to be inspected is picked up by a television camera, becomes different from a condition, where a reference body is picked up by the camera, due to variation of light irradiating the object, the electrical circuit system including the camera and so on, and the video signal from the camera corresponding to the object becomes different from that corresponding to the reference body not caused by the object itself but by the difference between the circumferential conditions therebetween, this variation of the video signal is automatically corrected and an erroneous judgement caused by the above variation of the video signal can be avoided by such a manner that a calibration body is located within the visual field of the television camera for the reference body and/or object to be inspected, a calibration signal is provided from the video signal corresponding to the calibration body and the video signal from the camera is corrected by the calibrating signal before the video signal is applied to a computer. Accordingly, with the present invention it is unnecessary to use an expensive light source with less variation of light amount or intensity, a light shielding device which will severely avoid any variation of the light from the light source to an object to be inspected and an expensive television camera having less drift, so that the cost of the inspection apparatus can be reduced while its accuracy can be greatly improved.

In the illustrated example of the invention, the calibration body 5 is located on the inspection table T in a position which is desirably within the visual field of the camera 3 where it will not hinder its picking up a reference and/or calibration body and where it can be kept unchanged throughout the picking up of the reference body and/or calibration body.

Further, it is also unnecessary that the calibration body 5 be limited to a white paper. The color thereof can be selected, for example, gray, yellow or the like within the scope to achieve the above purpose of the invention. Also, no limitation is required on the material forming the calibration body 5 if the material is capable of keeping its color unchanged. It will also be apparent that no limitation is necessary on the shape of the calibration body if it will not interfere with picking up a reference body and/or calibration body by the television camera.

Further, it is also possible that the correction of a video signal maybe carried out using the software of a programmed digital computer instead of the hardware recited in the above examples of the inventions.

It will be apparent that many modifications and variations could be effected by one skilled in the art without departing from the spirit or scope of the novel concepts of the present invention, so that the spirit or scope of the invention should be determined by the appended claims only.

I claim as my invention:

1. An object inspection apparatus comprising:
   (a) image sensing means having a visual field for producing a video signal responsive to objects in said visual field;
   (b) a calibration body in said visual field;
   (c) a reference body in said visual field, said reference body being substantially identical to said object;
   (d) means for normalizing at least the portion of said video signal which is responsive to said reference body according to a portion of said video signal which is responsive to said calibration body to produce a normalized reference signal;
   (e) means for storing said normalized reference signal;
   (f) means for permitting replacement of said reference body with said object;
   (g) said means for normalizing being further operative for normalizing at least the portion of said video signal which is responsive to said object according to a portion of said video signal which is responsive to said calibration body to produce a normalized object signal, whereby said normalized object signal is independent of changes in said image sensing means; and
   (h) means for comparing said normalized object signal with the stored normalized reference signal to judge whether or not said object corresponds to said reference body.

2. An inspection apparatus as claimed in claim 1, in which said image sensing means is a television camera.

3. An inspection apparatus as claimed in claim 1, in which said means for normalizing includes an A/D converter, a calibration signal forming circuit and a correcting circuit.

4. An inspection apparatus as claimed in claim 3, in which said A/D converter is supplied with the video signal from said image sensing means and is operative to convert said video signal to a digital video signal, said calibration signal forming circuit is supplied with said video signal and is operative to produce a calibration signal based upon the signal corresponding to said calibration body, and said correcting circuit is supplied with said digital video signal from said A/D converter and said calibration signal from said calibration signal forming circuit and is operative to normalize the former signal in response to the latter signal.

5. An inspection apparatus as claimed in claim 3, in which said calibration signal forming circuit is supplied with the video signal from said image sensing means and is operative to produce a calibration signal, said correcting circuit is supplied with the video signal from said image sensing means and the calibration signal from said calibration signal forming circuit and is operative to normalize said video signal in response to said calibration signal and said A/D converter is supplied with a normalized output video signal from said correcting circuit.

6. An inspection apparatus as claimed in claim 1, in which said calibration body, and at least one of said reference body and said object are located on a common inspection table within said visual field of said image sensing means and irradiated by the light from a light source.

* * * * *